United States Patent
Boettger et al.

(10) Patent No.: US 8,699,823 B2
(45) Date of Patent: Apr. 15, 2014

(54) METHOD AND DEVICE FOR REGISTERING MEDICAL IMAGE DATA

(75) Inventors: Thomas Boettger, Heidelberg (DE); Mark Hastenteufel, Heidelberg (DE)

(73) Assignee: Siemens Aktiengesellschaft, München (DE)

( * ) Notice: Subject to any disclaimer, the term of this patent is extended or adjusted under 35 U.S.C. 154(b) by 325 days.

(21) Appl. No.: 13/118,524

(22) Filed: May 30, 2011

(65) Prior Publication Data

US 2012/0134562 A1 May 31, 2012

(30) Foreign Application Priority Data

May 31, 2010 (DE) .......................... 10 2010 022 266

(51) Int. Cl.
*G06K 9/32* (2006.01)
(52) U.S. Cl.
USPC ............................... 382/294; 128/922; 378/4
(58) Field of Classification Search
USPC ......... 382/100, 128, 129, 130, 131, 132, 294, 382/295; 128/922; 378/4–27; 345/619–689
See application file for complete search history.

(56) References Cited

U.S. PATENT DOCUMENTS

| | | | | |
|---|---|---|---|---|
| 6,611,615 | B1 * | 8/2003 | Christensen | 382/130 |
| 6,625,332 | B1 * | 9/2003 | Nakao | 382/294 |
| 7,106,891 | B2 * | 9/2006 | Wyman et al. | 382/128 |
| 7,840,093 | B2 * | 11/2010 | Fu et al. | 382/294 |
| 2006/0165267 | A1 * | 7/2006 | Wyman et al. | 382/128 |
| 2008/0044104 | A1 * | 2/2008 | Gering | 382/294 |
| 2009/0091567 | A1 | 4/2009 | Fu et al. | |
| 2009/0213034 | A1 * | 8/2009 | Wu et al. | 345/1.1 |
| 2009/0228299 | A1 * | 9/2009 | Kangarloo et al. | 705/2 |
| 2010/0027911 | A1 * | 2/2010 | Lefebvre et al. | 382/294 |

FOREIGN PATENT DOCUMENTS

WO WO 2008/062415 A2 5/2008

OTHER PUBLICATIONS

German Office Action dated Apr. 15, 2011 for corresponding German Patent Application No. DE 10 2010 022 266.6-35 with English translation.

* cited by examiner

*Primary Examiner* — Anand Bhatnagar
(74) *Attorney, Agent, or Firm* — Lempia Summerfield Katz LLC

(57) ABSTRACT

The present embodiments relate to a method for registering medical image data. The method includes providing a registration parameter set for each of a plurality of different application cases, each of the plurality of different application cases being defined by at least one feature. Each registration parameter set contains registration parameters predefined for the associated application case. The method also includes providing first image data and second image data, which are to be registered onto one another. In response to the specification of an application case for the first image data and the second image data to be registered, a registration parameter set is automatically selected from the provided registration parameter sets in accordance with the specified application case. The method includes automatically performing a registration of the first image data onto the second image data using the selected registration parameter set.

23 Claims, 5 Drawing Sheets

FIG 6
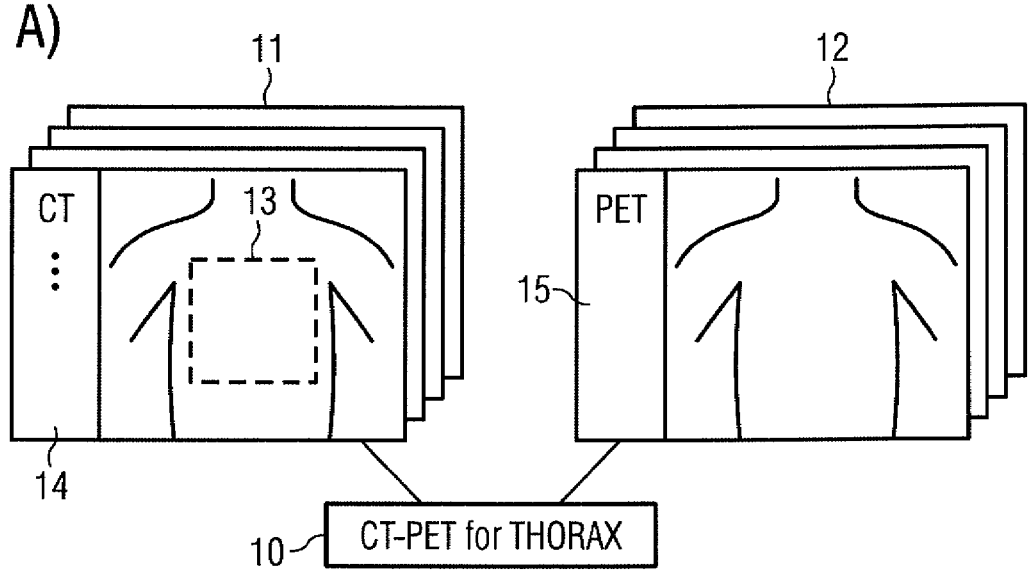
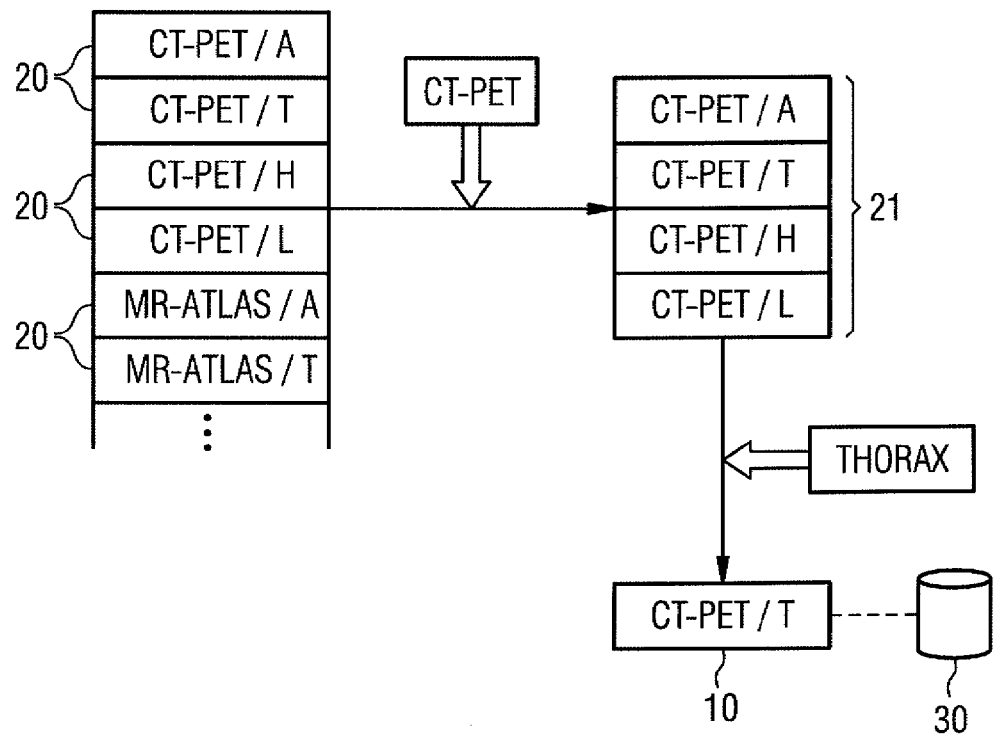

METHOD AND DEVICE FOR REGISTERING MEDICAL IMAGE DATA

This application claims the benefit of DE 10 2010 022 266.6, filed May 31, 2010.

BACKGROUND

The present embodiments relate to a device and method for registering medical image data.

Modern-day medical engineering technology provides a plurality of imaging modalities for visualizing regions of a body of a patient including internal tissue structures. Thus, for example, two-dimensional sectional images (slices) or three-dimensional volumetric images of regions of the body may be recorded using computed tomography (CT) or magnetic resonance tomography (MRT). When these technologies are used, acquired sets of image data may be compared with one another (e.g., the image data of the same patient acquired using different imaging techniques, image data of the patient with reference image data or image data of time series, of a beating heart, for example, or before and after therapeutic interventions).

Image registration methods are used in order to enable different image data of one or more patients to be displayed collectively and analyzed in a direct comparison. In the process, the image data to be compared is integrated and transformed into a common coordinate system. Where two image data sets are to be registered onto one another, one may be designated as a reference image R and the other as a model image M. The objective during the registration is to find the optimal transformation between the model image and the reference image. The optimal transformation may maximize a similarity metric of transformed model image and reference image. The optimization problem is solved using a registration algorithm.

The areas of application of automatic image registration encompass the combination of information from two or more imaging modalities for visualization or quantification, the combination of preoperative images with images acquired during an operation for the purpose of computer-assisted surgery, motion detection through registration of a time series of image data, automatic segmentation through registration onto pre-segmented anatomical atlases, and support for the planning of and treatment using radiotherapy. The requirements to be fulfilled by the registration algorithms are correspondingly diverse. In order to support robust automatic registration in clinical application, a registration algorithm specially tailored to the corresponding application is provided in conventional systems, the parameterization of the algorithm being defined for the specific registration problem. The registration functionality is accordingly specified for a specific organ, a specific anatomical structure or a specific region of the body, as well as for the specific registration problem (e.g., a specific imaging modality).

The application of a conventional registration method configured in this way to other than the explicitly specified registration problem and the specified image contents leads to a lack of robustness in the method as well as to a lack of precision in the registration and to misregistrations. Manually setting registration parameters in order to circumvent the problem may be out of the question, since setting by trial and error is very time-consuming and seldom leads to success. Often the clinical staff does not possess the technical knowledge to carry out such settings in relation to the registration algorithm.

SUMMARY AND DESCRIPTION

It would be desirable to achieve a high degree of precision in an image registration for different application cases. A user of such a registration method may not change registration parameters manually in order to increase the precision of the registration.

The present embodiments may obviate one or more of the drawbacks or limitations in the related art. For example, an improved method and device for registering medical image data may be provided.

In one embodiment, a method for registering medical image data is provided, where a registration parameter set is used for registering first image data onto second image data using a registration algorithm. According to the method, a registration parameter set is provided for each of a plurality of different application cases. An application case is defined by at least one of the following features: an acquisition property of the image data to be registered, content of the image data to be registered, or a selected region in the image data, onto which the registration is to be directed. Each registration parameter set contains registration parameters predefined for the associated application case. The method also includes providing first image data and second image data, which are to be registered onto one another. In response to the specification of an application case for the first image data and the second image data, which are to be registered, a registration parameter set is automatically selected from the provided registration parameter sets in accordance with the specified application case. The first image data is automatically registered onto the second image data using the selected registration parameter set.

As a result of the automatic selection of a registration parameter set in accordance with the specified application case, a precise and robust registration of image data having different acquisition properties or different contents may be provided using the method. With this solution, the application case may be specified manually, semi-automatically or automatically (e.g., through specification of the features defining the application case). By virtue of the specification of the application case and the corresponding automatic selection of the registration parameters, a technically untrained user may achieve good registration results for different application cases, since the user is relieved of the task of manually setting registration parameters. Since an optimal algorithm and an optimal parameter set may be used for each application case, an improvement in the registration result is possible. The registration is also completed more quickly because fewer user inputs are necessary. A registration may be performed for a wide range of clinical application cases using the method. The image data may include both two-dimensional (2D) and three-dimensional (3D) image data sets. The image data may also include a 4D registration of image data sets of a time series.

In one embodiment, an acquisition property of the image data to be registered may be, for example, one of the following: one or more of the imaging modalities used for generating the image data that is to be registered, protocol information of the imaging method used for generating the image data to be registered, a quality feature of the image data (e.g., a signal-to-noise ratio), contrast in the image data or a resolution of the image data. These are properties of the image data that are influenced by the acquisition method used. The content of the image data to be registered is determined, for example, by a region of the body imaged by the image data to be registered (or the imaged field of view (FOV)) or by an anatomical structure imaged in the image data, and onto which the registration is to be directed. Features of a selected region in the image data may be, for example, position, size or imaged content of the selected region. The selected region (e.g., a region of interest (ROI)) may be defined using a user input prior to the registration. A further feature of an application case may be the type of registration that is to be performed. An application case may be defined by one or a combination of the features. The application case may be precisely defined by the cited features, so that a registration parameter set containing corresponding registration parameters specified for the application case enables a robust and precise registration. The method allows the precise specification of the application case and consequently the use of better configured registration parameters that may lead to a better registration result and to faster registration owing to better initialization values.

The type of registration to be performed (e.g., image registration) may be, for example an atlas-based segmentation, a multimodal registration (image fusion), a structure-oriented image data interpolation (temporal and/or spatial), a motion detection or an estimation of motion fields.

According to an embodiment, the method also includes the automatic specification of at least one feature of the application case for the first image data and the second image data to be registered, the feature being determined by an analysis of the first image data and/or the second image data. Automatic specification of at least one feature of the application case relieves the user further of user inputs and speeds up the method. By virtue of the automatic specification, the user may be supported in determining the application case, which is advantageous, for example, with regard to such features that the user may determine only with difficulty or that are laborious and time-consuming to input (e.g., parameters of the imaging method used).

The automatic specification of the feature may include, for example, the automatic determination of an acquisition property of the first image data and the second image data (e.g., the imaging modalities or imaging protocol parameters used for generating the first image data and the second image data). The analysis of the first image data and/or the second image data for determining the acquisition property of the image data may be conducted by reading out a header of the first image data and/or the second image data. The digital imaging and communications in medicine (DICOM) header may thus be read out. A header may also be referred to as a header field of a file or data frame. Certain important features of the application case may already be determined automatically and in a simple manner.

The automatic specification of the at least one feature may include the automatic determination of content of the first image data or the second image data (e.g., a region of the body or anatomical structure imaged in the first image data or the second image data and onto which the registration is to be directed) by analysis of the first image data and/or the second image data. This also relieves the user of user inputs and leads to faster performance of the registration method. The analysis of the first image data and/or the second image data for determining the content of the image data may be carried out using an image detection method that detects at least the presence of an anatomical structure in the image data. This may involve, for example, "image tagging" techniques, in which an automatic detection of anatomical landmarks takes place so that the presence of a particular organ may be detected in the image. Atlas-based methods that detect the presence of certain organs in the data set using an atlas of the entire human body may also be used. Recourse may also be made, for example, to methods that are used in content-based image retrieval (CBIR).

Further features already specified (automatically or manually) may be referred to in order to improve the detection (e.g., the cited acquisition properties).

In one embodiment, the method executes fully automatically. The method includes the automatic specification of the application case for the first image data and the second image data to be registered based on automatic determination of all features of the application case by an analysis of the image data. The features provided in this instance for the definition of the application case may be preset by default, for example, or specified by a user. In one embodiment, the features include at least the imaging modalities used for generating the image data and also the image content of the image data to be registered. A precise and robust registration of the image data may be realized without further user input. The method may perform the registration solely based on the image data. In addition to the increased registration precision, the duration of the method may be further reduced as a result of the avoidance of user inputs.

In another embodiment, the method includes the specification, by a user input, of at least one feature of the application case for the first image data and the second image data to be registered. An application case may therefore also be precisely defined for features that may be determined automatically by a higher investment of effort.

The specification of a feature by a user input may be effected, for example, by a display of application cases for different instances of the feature to be specified, for which a registration parameter set is provided, and selection of an application case according to the instances of the feature from the displayed application cases by the user input. If the feature relates, for example, to the imaging modality, and if registration parameter sets for application cases with different instances of the feature are available (e.g., "CT", "MRT", or positron emission tomography ("PET")), then the application cases may be offered for selection. Simple and intuitive input of the respective application case is made possible in this way. A corresponding approach may be adopted for feature combinations. Thus, for example, all the features of an application case to be defined may be specified by a single selection.

In one embodiment, at least one feature of the application case for the first image data and the second image data is determined automatically by analysis of the first image data and/or the second image data, such application cases that have the automatically determined feature being specifiable by a user input. Such a semi-automatic specification of the application case makes the method faster and simplifies the selection of the features for the user. Thus, for example, it may be determined automatically that the first image data was acquired using CT and the second image data using PET; only such application cases having the feature "CT-PET" may then be offered for selection.

Following the specification of the application case, the automatic selection may take place, for example, such that the registration parameter set having an associated application case that has the most features consistent with the specified application case is selected. In one embodiment, the registration parameter set having the associated application case that has all the features of the specified application case is selected. Depending on the number of features defined for the specified application case, a corresponding parameter set may not be present. In this case, the registration parameter set having the most features in common may then be used.

A feature of the application case associated with a registration parameter set may also be defined by a range. If instances of a feature of the specified application case falls within the range, a correspondence with respect to the feature may be assumed.

A registration parameter set may include, for example, at least one or a combination of the following registration parameters: a selection parameter that determines a registration algorithm to be used; initialization parameters for initializing the registration algorithm; parameters for restricting the search space of the registration algorithm; parameters for determining a quality metric of the registration algorithm; parameters for defining stop values for the registration algorithm; regularization parameters for the registration algorithm; selection parameters for selecting a geometric transformation; parameters for parameterizing an optimization method, and parameters for parameterizing an interpolation method. Additional parameters may also be incorporated. The selection parameters may define, for example, whether an algorithm is to be used for a rigid registration or for a registration with deformation of the image data.

The method may also include an automatic adjustment of a registration parameter of the selected registration parameter set according to the instance of a feature of the specified application case. For example, if the specified application case defines a specific position of a region of interest (ROI), an initialization parameter for the registration algorithm may be adjusted accordingly, for example (e.g., for initializing a displacement transformation or another type of transformation).

The registration parameters may also be manually adjusted. The method may also include the storing of modifications to a registration parameter that are made during the performance of the registration method as a result of manual setting of the registration parameter set for the corresponding registration parameter set, as well as the adjustment of the registration parameter of the registration parameter set in accordance with the modifications stored for the registration parameter set. The parameter may be set, for example, to the average value for a specific number of modified parameter settings. This enables manual parameter adjustments to be logged, and the registration parameter set may be trained for the corresponding application case using the logged parameter modifications.

The methods described above may be performed automatically by a computer unit, for example, using a program that executes on the computer unit. The program may provide the registration parameter sets, for example, by accessing a database, in which the sets are stored in conjunction with the associated application cases (e.g., the features defined for the application cases).

In one embodiment, a device for registering medical image data is provided. The device for registering medical image data is configured for using a registration parameter set to perform a registration of first image data onto second image data using a registration algorithm. The device includes a parameter memory unit, in which a registration parameter set is stored for each of a plurality of different application cases, an application case being defined by at least one of the following features: an acquisition property of the image data to be registered, content of the image data to be registered, or a region of interest in the image data, onto which the registration is to be directed. Each registration parameter set contains registration parameters predefined for the associated application case. The device also includes an image memory unit that is configured for storing first image data and second image data that are to be registered onto one another (where the data may also be stored only temporarily), and a selection unit that is configured for automatically selecting, in response to the specification of an application case for the first image data and the second image data to be registered, one registration parameter set from the registration parameter sets stored in the parameter memory unit in accordance with the specified application case. The device includes a registration unit that is configured for automatically performing a registration of the first image data onto the second image data using the registration parameter set selected by the selection unit.

Similar advantages to those described above may be achieved using the device according to the present embodiments.

In one embodiment, the device is configured for performing one of the above-described methods.

The present embodiments also provide a non-transitory electronically readable data medium, on which electronically readable control information is stored. The electronically readable control information is configured such that the electronically readable control information performs one of the above-described methods when the data medium is used in a computer system. Also provided is a computer program product including a computer program that performs one of the above-described methods when executed in a computer system.

The features of the above- and below-described embodiments may be combined with one another.

BRIEF DESCRIPTION OF THE DRAWINGS

FIGS. 6A and 6B illustrate the specification of an application case for the registration of first and second image data.

DETAILED DESCRIPTION OF THE DRAWINGS

The purpose of a registration method is to find a transformation that accurately correlates first image data (e.g., model image) with second image data (e.g., reference image). This may include a combination of simple rigid transformations or more complex transformations that, for example, assign a one-dimensional or multidimensional displacement to each image pixel or voxel. Whereas the shape of imaged organs remains the same in the first-mentioned case, the shape may change in the second-mentioned case due to the transformation (e.g., deformable registration). As a result of the shape change, an atlas-based segmentation is made possible. By determining the transformation between an image to be segmented and an atlas image using the registration, a segmentation available for the atlas image may be transferred back onto the image to be segmented. Intra-individual registration is also a frequent application, where a fusion of image data acquired using different examination modalities for the same patient takes place. Using the registration method, MRT images that may visualize soft tissue with considerable contrast, or CT images may be overlaid with PET images, in which metabolic processes may be made visible, for example. A registration may be performed both for two-dimensional layer images and for a three-dimensional image data set. A 4D registration, where a temporal sequence of 3D image data sets is recorded (3D+t), may also be performed. The temporal sequence of 3D image data sets may be registered onto one another (e.g., in dynamic CT images). The same applies to time series of 2D image data (2D+t), in which a registration of 2D image data acquired at different points in time is performed.

Figure 1:
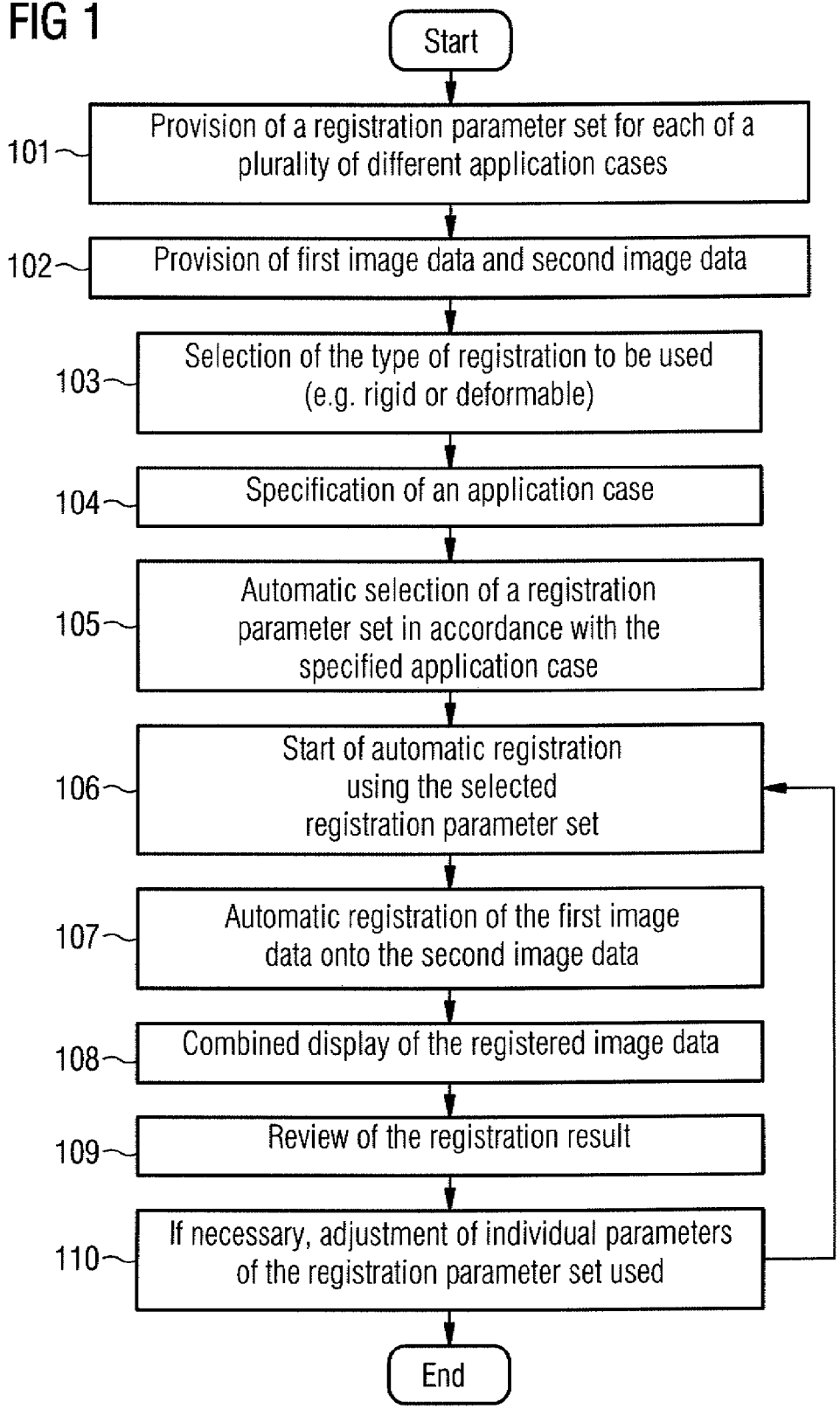
FIG. 1 shows a flowchart of one embodiment of a method for registering medical image data.
Figure 2:
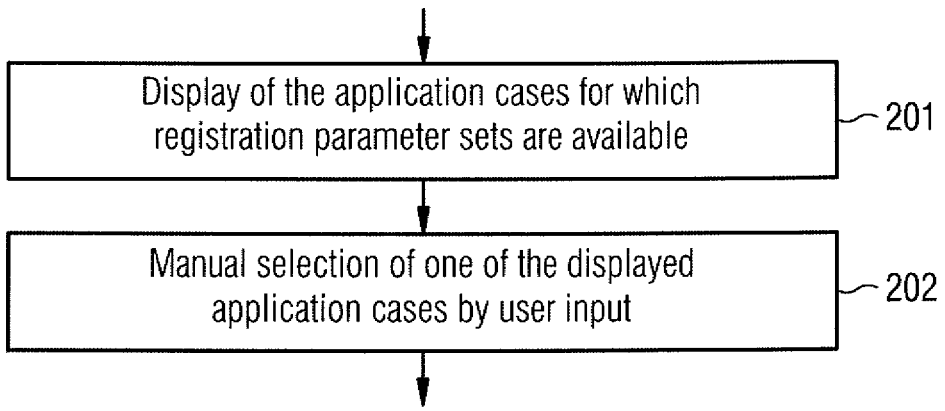
FIG. 2 shows a flowchart of one embodiment of a method for specifying an application case.
Figure 3:
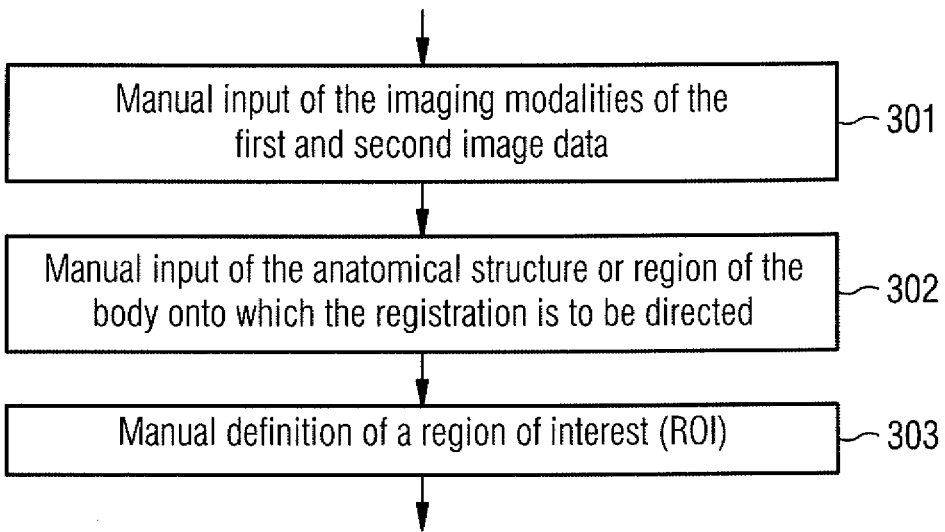
FIG. 3 shows a flowchart of one embodiment of a method for specifying an application case.
Figure 4:
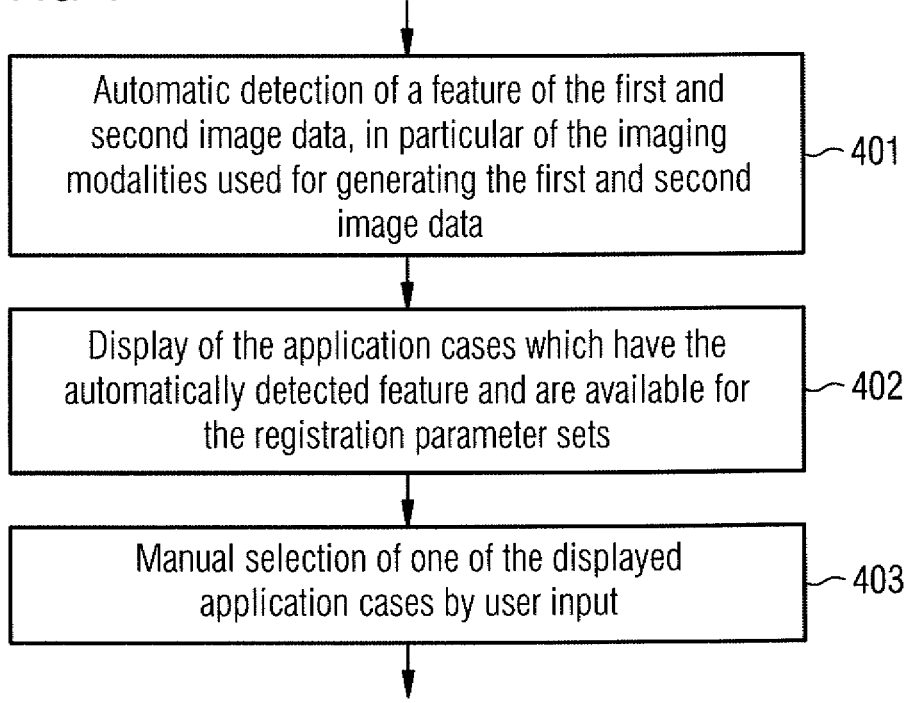
FIG. 4 shows a flowchart of one embodiment of a method for specifying an application case.

With the registration method illustrated in FIG. 1, a precise and robust registration of the image data may be achieved for different types of registration problems. A registration parameter set is provided in act 101 for each of a plurality of different application cases. An application case may be defined by different features that may have an effect on the image registration. The different features include, for example, imaging modalities used for generating the image data to be registered, imaging protocol information, a quality of the image data (e.g., a signal-to-noise ratio), a contrast in the image data, a resolution of the image data, and similar. Registration parameter sets may be provided for the registration of image data for CT on CT, CT on PET, or MR on PET, for example. The application case may also be determined by image content of the image data to be registered. Image-content-related features may be, for example, an imaged field of view or a region of a body imaged in the image data, an imaged anatomical structure, onto which the registration is to be directed, or similar content-related features. Examples of application cases include the registration of image data of the thorax or abdomen of an examination subject or the registration of an organ imaged in the image data, such as the heart, lung or liver, where less consideration is given to other structures in the image data in the case of such a targeted registration.

In one embodiment, the application ease may be a selected region or region of interest that a user specifies in the image data and onto which the registration is to be directed. If only a section of the imaged field of view is significant for the registration problem, the user may mark the section in order to focus the registration on the section. The registration may take into account only the image contents within the regions of interest. The region of interest may be specified, for example, either in the model image or in the reference image. Alternatively, the region of interest may be specified in the model image and the reference image.

In one embodiment, the application case may include a type of registration that is to be performed. The type of registration may include, for example, atlas-based segmentation, multimodal registration, structure-oriented image data interpolation, or motion detection. The type of registration to be performed may influence the registration algorithm to be used and specify, for example, whether a rigid or a deformable registration is to be performed.

The application case is defined by one or a combination of more than one of the cited features. This is illustrated by way of example in FIG. 6B, which shows several application cases 20. A registration parameter set is provided for each of the application cases 20. Listed here by way of example are application cases for a registration of CT and PET image data, as well as MRT and atlas image data, where atlas images may be constructed from MRT images of a plurality of different examination subjects. In FIG. 6B, registration parameter sets for different image contents are also provided for each modality (e.g., for an image registration directed onto the abdomen (A), the thorax (T), the heart (H) or the lung (L)). A limited number of exemplary application cases are shown in FIG. 6B. The application cases may be defined by considerably more features, and registration parameter sets may be provided for considerably more than the shown instances of the features.

Referring again to FIG. 1, the first image data and the second image data are provided in act 102. The first image data and the second image data are illustrated by way of example in FIG. 6A. The first image data 11 includes a set of two-dimensional layer images (e.g., a three-dimensional image data set) acquired using computed tomography. The set of two-dimensional layer images visualize the thorax of an examination subject. The first image data 11 includes a header 14, in which protocol information of the imaging method is stored. The header may be, for example, a DICOM header. Also shown in the first image data 11 is a region of interest 13 specified by a user. The second image data 12 essentially images the same region of the body (e.g., the thorax of the examination subject) and includes a header 15. The second image data 12 includes a plurality of two-dimensional layer images and constitutes a three-dimensional layer image set.

The first image data 11 and the second image data 12 to be registered on one another with given image contents and acquisition properties specify a particular registration problem that may be defined by an application case 10. For the image data illustrated in FIG. 6A, the application case may be defined by "registration of CT and PET image data for the thorax." Further features may be included for the definition of the application case 10, such as through definition of image quality features or the region of interest 13, for example.

After the image data has been provided, the registration type (e.g., rigid or deformable) is selected in act 103 of the flowchart of FIG. 1. The registration type may be preselected manually. In one embodiment, the type of registration may be defined in the application case. Registration parameter sets are provided for each of the different registration types so that a preselection from the available sets may be made by specification of the registration type. In one embodiment, the registration type to be used may automatically be determined based on the remaining features of the application case.

The specification of an application case takes place in act 104. The application case to be specified may be determined by the registration problem and by the provided first image data 11 and the second image data 12. The application case may be specified manually, semi-automatically or fully automatically, as explained in more detail below with reference to FIGS. 2-5. The application case 10 illustrated in FIG. 6A may be specified by manual input of "CT-PET" and "Thorax," for example, by manual selection of one of the provided application cases 20, or one or both features may be determined automatically from the first image data 11 and/or the second image data 12 by an analysis thereof.

A registration parameter set corresponding to the specified application case is automatically selected in act 105. In an automatic determination of the features of the application case from the provided first image data 11 and second image data 12, a search may be conducted for one of the application cases 20 having the automatically determined features, or having a maximum correlation with the automatically determined features. If the specified application case 10 defines fewer features than the provided application cases 20, a plurality of found application cases 20 may be offered for selection as alternatives.

A similar procedure may be followed for a manual specification of individual features of the application case. In one embodiment, application cases, for which registration parameter sets are also available, may be offered directly for selection, with the result that a search may be dispensed with.

Using a manual selection, for example, the user may directly specify the application case with all features or specify the individual features in turn. The corresponding registration parameter set may thus be determined and selected.

In act 106, the registration of the first image data 11 and the second image data 12 is started using the selected registration parameter set. The automatic registration may be triggered manually, for example, by a user input or directly following the selection of the parameter set. The registration parameter set may define a registration algorithm to be used. The registration parameter set may also contain parameters for initializing and conditioning the registration algorithm. The parameters for initializing and conditioning the registration algorithm include, for example, parameters for limiting the search space, for defining a quality metric or a requisite registration precision, stop values or abort values for the registration algorithm, and/or regularization values.

The automatic registration of the first image data 11 onto the second image data 12 takes place in act 107. The registration result is displayed in act 108. As a check, the result may be reviewed by a user in act 109. In act 110, the user may adjust individual parameters of the registration parameter set used. The cases, in which such manual adjustments are made, are reduced through the provision of the registration parameter sets for different application cases. In act 106, a re-registration of the provided image data is performed using the modified registration parameter set. If no adjustment is to be made, the method illustrated in FIG. 1 is terminated.

Further method acts that for clarity of illustration are not shown in FIG. 1 may be performed before, during and/or after the registration method. The further method acts include conventional registration method acts and also variations of the method shown in FIG. 1. For example, the adjustment of individual parameters in act 110 may be stored (or logged) in order to implement training of the registration parameter sets based on the stored adjustments. For a particular application case, for which an adjustment of the parameters may be performed, the parameters predefined in the associated parameter set may be modified accordingly in order to avoid such adjustments. The parameter set may be optimized for the specific application case. Methods for training a parameter set are known to the person skilled in the art, so the methods for training a parameter set will not be discussed in greater detail here.

The flowcharts shown in FIGS. 2-5 show examples illustrating how an application case may be specified in act 104 of FIG. 1. In the embodiment shown in FIG. 2, the application cases, for which registration parameter sets are available, are displayed in the first instance (act 201). For example, the available application cases 20 are displayed, as illustrated in FIG. 6B, in the form of a list or similar. In act 202, one of the displayed application cases 20 is manually selected through user input using an input unit that may include a keyboard and a mouse, for example. For the first image data 11 and the second image data 12 shown in FIG. 6A, the user selects the application case CT-PET/T (e.g., for Thorax). Multiple features of the application case to be specified may be defined by a single input.

Given a plurality of possible instances of the features, or if the application cases are defined by a plurality of features, such lists may be considerably long. In order to simplify the input, in the embodiment shown in FIG. 3, the application case is specified by manual specification of the individual features. The imaging modalities used for generating the first image data 11 and the second image data 12 are initially input manually in act 301. This may be accomplished by way of a selection list of the possible imaging modalities, for which registration parameter sets are available, or directly through text-based input or a similar process. In the example of FIG. 6, the input "CT-PET" is made for the first image data 11 and the second image data 12 to be registered, as indicated by an arrow in FIG. 6B. This leads to a reduced selection list 21 including the available application cases that have the corresponding feature (e.g., which are provided for the registration of CT onto PET image data).

Manual input of the anatomical structure or the region of the body, onto which the registration is to be directed, takes place in act 302. The region of the body represented in the first image data 11 and the second image data 12 may be specified, for example, or an organ imaged in the first image data 11 and the second image data 12, onto which the registration is to be focused (e.g. for a segmentation of the corresponding organ) may be specified. The manual input may be realized by a selection from the reduced list 21 of possible available application cases, by text-based input or in some other way. For the example shown in FIG. 6, images of the thorax are to be registered on top of one another, so the manual input "Thorax" is made, as indicated by arrows. Thus, the application case 10 (e.g., CT-PET/T) is specified. The associated registration parameter set 30 may be automatically selected for the purpose of performing automatic image registration. If a plurality of application cases 20 having all the features of the specified application case 10 is provided, the plurality of application cases 20 may be presented to the user for selection. Alternatively, the user may define further features.

For example, a region of interest (ROI) may be defined manually in act 303, as indicated by reference sign 13 in FIG. 6A. Corresponding registration parameter sets containing registration parameters configured for the corresponding region of interest may be provided for different positions, sizes or image contents of the region of interest. The parameters of the selected registration parameter set 30 may be adjusted based on the defined region of interest.

The above-described input of the features of the application case 10 may also be effected automatically each time. The features to be specified automatically may be determined by an analysis of the image data to be registered. In the example shown in FIG. 4 for specifying an application case, a feature of the first image data 11 and the second image data 12 (e.g., the imaging modalities used for generating the first image data and the second image data) or protocol parameters of the corresponding imaging protocol are automatically detected in act 401. The feature of the first image data 11 and the second image data 12 and the protocol parameters of the corresponding imaging protocol may be obtained by reading out the headers 14 and 15 of the first image data 11 and the second image data 12, respectively. Medical image data may be provided with a DICOM header, in which appropriate information is stored. In addition to the modalities used, information relating to quality features of the image data such as, for example, a resolution, a pixel spacing, a layer thickness, and similar may be obtained in the DICOM header. If the application case to be specified is defined only by the automatically detected feature, the automatic selection of a corresponding registration parameter set 30 may take place immediately. In the example shown in FIG. 4, a further feature is defined manually in addition to the automatically detected feature (e.g., semi-automatic specification of the application case). For this purpose, the application cases that have the automatically detected feature and, for which registration parameter sets are available, are displayed in act 402. This may be effected, as illustrated in FIG. 6B, using the reduced selection list 21. One of the displayed application cases is selected using a user input in act 403. This leads, as described above, to the specification of the application case 10.

Figure 5:
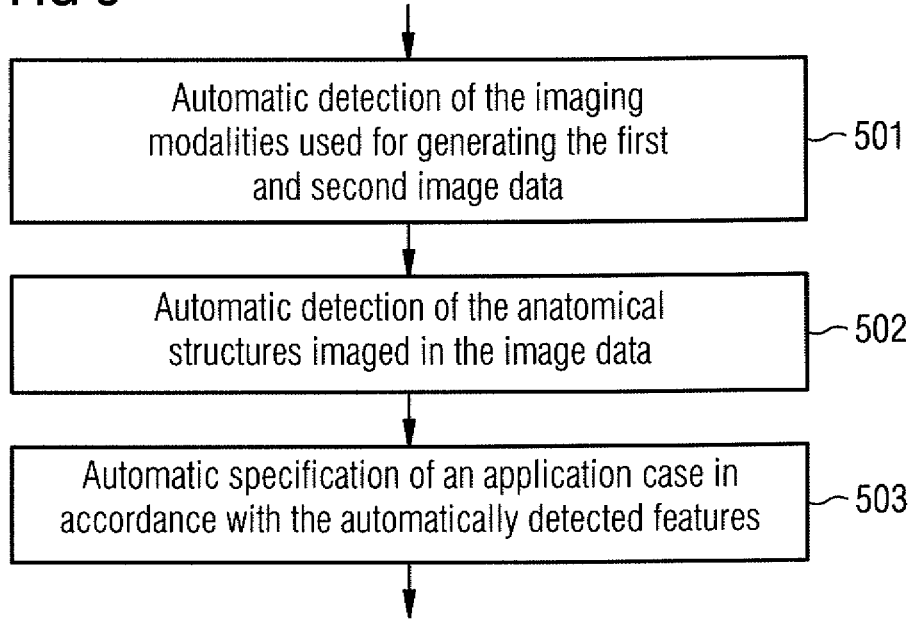
FIG. 5 shows a flowchart of one embodiment of a method for specifying an application case.

FIG. 5 shows a flowchart with a fully automatic specification of the application case. For this purpose, the imaging modalities used for generating the first image data 11 and the second image data 12 are automatically detected in act 501. A further feature of the application case is specified automatically through analysis of the image content of the image data to be registered. The use of correspondingly adjusted registration parameters is advantageous for a precise and robust registration of different regions of the body. The automatic detection of the anatomical structures imaged in the image data takes place in act 502. This may be realized using an image detection method that detects the presence of specific anatomical structures in the image data. Simple methods (e.g., "image tagging") may be employed to detect the presence of a specific organ in the image data to be registered. In addition, certain anatomical landmarks may be detected automatically in the image data. The presence of the certain anatomical landmarks allows inferences to be made about the content of the image data. The detection of positions of the certain anatomical landmarks allows further deductions to be made about the orientation of the image data, imaged regions and similar. A more precise automatic detection of image contents may be realized using atlas-based methods. A complete scan of the human body is used as a reference in conjunction with an atlas that contains all of the important organs and organ structures for the data set. In order to take into account variations between different individuals, an average atlas may be used. The average atlas may compute average organ shapes from a plurality of fully annotated data sets. The content of the image data to be registered may be determined by initially registering an image data set with the averaged atlas image. As a result, the presence as well as the position, shape and size of the organs formed in the image data set may be precisely determined.

Methods for detecting the image content that are known from the domain of content-based image retrieval may be employed. In content-based image retrieval, an analysis of the image content is conducted by an analysis of colors, contours, surfaces or textures, or of further information. Using methods of this type, which anatomical structure is imaged in the image data may also be ascertained.

A plurality of methods, using which the anatomical structures imaged in the image data to be registered may be detected automatically are available. In the example shown in FIG. 6, it may be automatically detected that the first image data 11 and the second image data 12 image the thorax of the examination subject and that a registration for the thorax is to be performed.

As a result of the automatic detection of the features "imaging modality" and "image content," the automatic specification of an application case may take place in act 305, a corresponding registration parameter set 30 being selected in accordance therewith. The image data may be registered using parameters specific to the detected image content and the detected imaging modalities. The precision and robustness of the automatic registration may consequently be significantly improved.

The application case 10 may be defined by the specification of more or fewer than the previously described features. The individual features of the application case may be specified either manually or automatically. Fully automatic specification of the entire application case 10 has the advantage that no further user inputs are necessary, and the registration method may therefore be performed more rapidly. This enables a simple, fast and highly efficient automatic registration of medical image data to be realized. Improved image registration is achieved both for application cases with deformable registration and for application cases with rigid registration. On the basis of the specified features, whether a rigid or deformable registration is to be performed may be specified by the automatically selected registration parameter set (e.g., a type of registration algorithm to be used).

Figure 7:
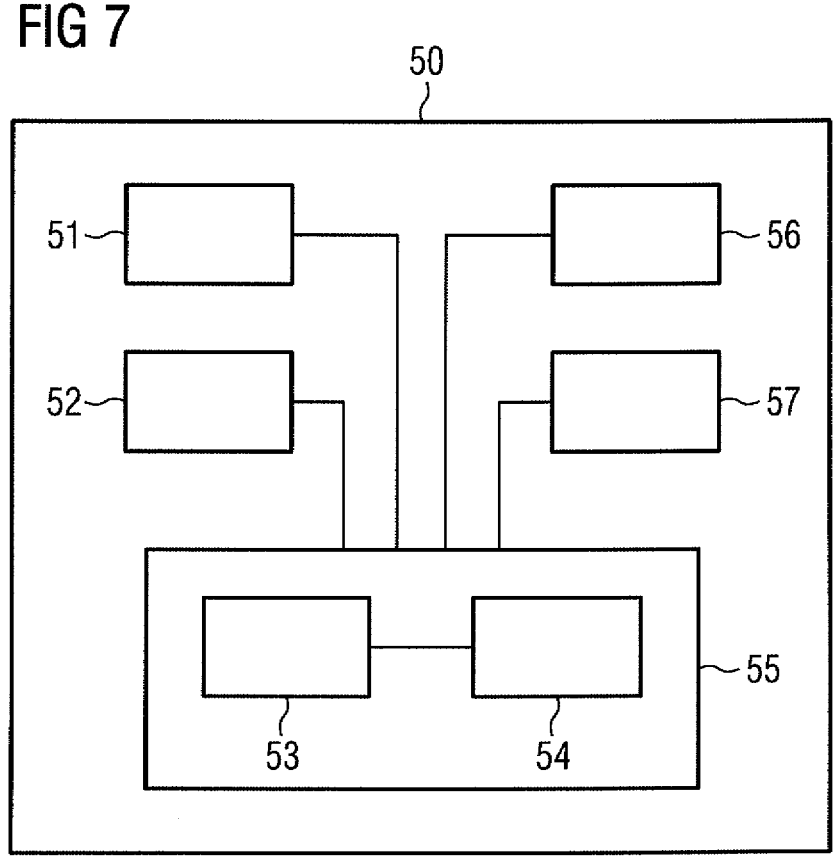
FIG. 7 is a schematic representation of one embodiment variant of a device for registering image data.

FIG. 7 schematically illustrates an embodiment a device for registering medical image data. The device 50 may be configured for performing one of the methods described above. The device 50 includes a parameter memory unit 51 that stores a plurality of registration parameter sets together with an associated application case for each registration parameter set of the plurality. The device 50 also includes an image memory unit 52 that stores the first image data and the second image data 12 to be registered. The device 50 may be configured to perform the image registration fully automatically.

A processing unit 55 is configured to determine features of the image data to be registered (e.g., acquisition properties and contents of the image data to be registered) automatically and to specify a corresponding application case automatically.

According to the specified application case, a selection unit 53 is configured to automatically select a registration parameter set from the parameter sets provided in the parameter memory unit 51. For example, the registration parameter set having an associated application case that has the most features consistent with the specified application case is selected. The selection unit 53 passes the selected registration parameter set to the registration unit 54, which uses the parameter set to perform an automatic registration of the first image data onto the second image data. The registration result may be displayed for review purposes on a display unit 56 as an overlay of a transformed model image and a reference image, for example, a user being able to make manual corrections to the registration parameters using an input unit 57.

The device 50 may also be configured for semi-automatic or manual specification of the application case. Certain features, for which application cases are available, for example, are provided for selection on the display unit 56, a user being able to make a selection using the input unit 57. One, more than one or all features of the application case may be specified using a user input, as explained above with reference to the corresponding methods.

The device 50 may be implemented as a computer unit (e.g., a computer system). The parameter memory unit 51 and the image memory unit 52 may include volatile or nonvolatile memory. The parameter memory unit 51 and the image memory unit 52 may also be provided by a single storage medium (e.g., a hard disk, a read-only memory, a RAM memory or similar). The processing unit 55 may be implemented as a microprocessor, on which appropriate control programs for implementing the selection unit 53 and the registration unit 54 execute. Control information of this type may be stored in a memory of the device 50 (e.g., on an electronically readable data medium).

The present embodiments enable precise and robust registration of medical image data for a plurality of different application cases. Because the application cases may be specified semi-automatically, automatically or manually, the method provides the advantage of great flexibility, such that the registration may be directed, for example, onto a specific organ or a specific region. The automatic determination of the features leads to a minimization of the number of user inputs and to faster performance of the method. Owing to the specification of a plurality of features, an application case may be precisely defined, enabling registration parameters specific to the corresponding registration problem to be provided by the method. As a result, a very precise as well as fast and robust registration may be performed.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for registering medical image data, the method comprising:
providing a registration parameter set for each application case of a plurality of different application cases, the registration parameter set being used for registering first image data onto second image data using a registration algorithm, the application case being defined by an acquisition property of image data to be registered, content of the image data to be registered or a region of interest in the image data, onto which the registration is to be directed, wherein each registration parameter set includes registration parameters predefined for an associated application case;
providing the first image data and the second image data, which are to be registered onto one another;
specifying an application case of the plurality of different application cases for the first image data and the second image data to be registered;
automatically selecting one registration parameter set from the provided registration parameter sets in accordance with the specified application case; and
automatically performing a registration of the first image data onto the second image data using the one selected registration parameter set.

2. The method as claimed in claim 1, wherein each application case of the plurality of different application cases is defined by one or more imaging modalities used for generating the first image data and the second image data to be registered, protocol information of an imaging method used for generating the first image data and the second image data to be registered, a quality feature of the first image data or the second image data, a region of a body imaged by the one or more imaging modalities used for generating the first image data or the second image data to be registered, an anatomical structure imaged by the one or more imaging modalities used for generating the first image data or the second image data to be registered and onto which the registration is to be directed, position, size or content of a region of interest in the first image data or the second image data, onto which the registration is to be directed, or a type of registration to be performed.

3. The method as claimed in claim 1, further comprising automatically specifying at least one feature of the application case for the first image data and second image data to be registered, the at least one feature being determined by an analysis of the first image data, the second image data, or the first image data and the second image data.

4. The method as claimed in claim 3, wherein automatically specifying the at least one feature comprises automatically determining an acquisition property of the first image data and the second image data through the analysis of the first image data, the second image data, or the first image data and the second image data.

5. The method as claimed in claim 4, wherein the analysis of the first image data, the second image data, or the first image data and the second image data for determining the acquisition property of the first image data and the second image data is conducted by reading out a header of the first image data, the second image data, or the first image data and the second image data.

6. The method as claimed in claim 4, wherein the acquisition property includes imaging modalities or imaging protocol parameters used for generating the first image data and the second image data.

7. The method as claimed in claim 3, wherein automatically specifying the at least one feature includes automatically determining content of the first image data or the second image data through the analysis of the first image data, the second image data, or the first image data and the second image data.

8. The method as claimed in claim 7, wherein the analysis of the first image data, the second image data, or the first image data and the second image data for determining the content of the first image data or the second image data is conducted using an image detection method that detects at least the presence of an anatomical structure in the first image data or the second image data.

9. The method as claimed in claim 7, wherein the content of the first image data or the second image data includes a region of a body or an anatomical structure imaged in the first image data or second image data and onto which the registration is to be directed.

10. The method as claimed in claim 1, further comprising automatically specifying the application case for the first image data and the second image data to be registered by automatic determination of all features of the application case by an analysis of the first image data and the second image data.

11. The method as claimed in claim 1, further comprising specifying, by a user input, at least one feature of the specified application case for the first image data and the second image data to be registered.

12. The method as claimed in claim 11, wherein specifying the at least one feature by the user input comprises displaying the plurality of different application cases for different instances of the at least one feature to be specified, for which the registration parameter set is provided, and
wherein specifying the application case comprises selecting the application case according to the instances of the at least one feature from the displayed plurality of different application cases by the user input.

13. The method as claimed in claim 11, further comprising automatically determining the at least one feature of the specified application case for the first image data and the second image data by analysis of the first image data, the second image data, or the first image data and the second image data.

14. The method as claimed in claim 1, wherein automatically selecting the one registration parameter set comprises selecting a registration parameter set with an associated application case that has the most features consistent with the specified application case.

15. The method as claimed in claim 14, further comprising defining a corresponding feature of the associated application case using a correspondence in a feature present when an instance of the feature of the specified application case falls within a range.

16. The method as claimed in claim 1, wherein each of the registration parameter sets includes a selection parameter that determines a registration algorithm to be used, initialization parameters for initializing the registration algorithm, parameters for restricting a search space of the registration algorithm, parameters for determining a quality metric of the registration algorithm, parameters for defining stop values for the registration algorithm, regularization parameters for the registration algorithm, selection parameters for selecting a geometric transformation, parameters for parameterizing an optimization method, or parameters for parameterizing an interpolation method.

17. The method as claimed in claim 1, further comprising automatically adjusting a registration parameter of the one selected registration parameter set according to an instance of a feature of the specified application case.

18. The method as claimed in claim 1, further comprising:
    storing modifications that are made to a registration parameter by manual setting of the registration parameter for a corresponding registration parameter set; and
    adjusting the registration parameter of the corresponding registration parameter set according to the stored modifications for the corresponding registration parameter set.

19. The method as claimed in claim 1, wherein the method is performed automatically by a program that executes on a computer unit.

20. The method as claimed in claim 1, wherein the quality feature is a signal to noise ratio, a contrast or a resolution of the first image data or the second image data.

21. A device for registering medical image data, the device comprising:
    a parameter memory unit configured to store a registration parameter set for each application case of a plurality of different application cases, the application case being defined by an acquisition property of the first image data and the second image data to be registered, content of the first image data and the second image data to be registered, or a region of interest in the first image data and the second image data, onto which the registration is to be directed, wherein each registration parameter set contains registration parameters predefined for an associated application case;
    an image memory unit configured for storing the first image data and the second image data, which are to be registered onto one another;
    a selection unit configured for automatically selecting, in response to the specification of an application case for the first image data and second image data to be registered, one registration parameter set from the registration parameter sets stored in the parameter memory unit in accordance with the specified application case; and
    a registration unit configured for automatically registering the first image data onto the second image data using the one registration parameter set selected by the selection unit.

22. In a non-transitory computer readable medium comprising computer readable instructions that, when executed by a computer system, register medical image data, the computer readable instructions comprising:
    providing a registration parameter set for each application case of a plurality of different application cases, the registration parameter set being used for registering first image data onto second image data using a registration algorithm, the application case being defined by an acquisition property of image data to be registered, content of the image data to be registered or a region of interest in the image data, onto which the registration is to be directed, wherein each registration parameter set includes registration parameters predefined for an associated application case;
    providing the first image data and the second image data, which are to be registered onto one another;
    specifying an application case of the plurality of different application cases for the first image data and the second image data to be registered;
    automatically selecting one registration parameter set from the provided registration parameter sets in accordance with the specified application case; and
    automatically performing a registration of the first image data onto the second image data using the one selected registration parameter set.

23. A computer program product comprising a non-transitory computer readable storage medium storing a computer program that, when executed by a computer system, registers medical image data, the computer program including instructions comprising:
    providing a registration parameter set for each application case of a plurality of different application cases, the registration parameter set being used for registering first image data onto second image data using a registration algorithm, the application case being defined by an acquisition property of image data to be registered, content of the image data to be registered or a region of interest in the image data, onto which the registration is to be directed, wherein each registration parameter set includes registration parameters predefined for an associated application case;
    providing the first image data and the second image data, which are to be registered onto one another;
    specifying an application case of the plurality of different application cases for the first image data and the second image data to be registered;
    automatically selecting one registration parameter set from the provided registration parameter sets in accordance with the specified application case; and
    automatically performing, by the computer system, a registration of the first image data onto the second image data using the one selected registration parameter set.

* * * * *